(12) United States Patent
Leibfritz et al.

(10) Patent No.: US 8,938,284 B2
(45) Date of Patent: Jan. 20, 2015

(54) MICROWAVE INVESTIGATION WITH A CONTRAST MEDIUM

(75) Inventors: Martin Leibfritz, Munich (DE); Gerd Hechtfischer, Vaterstetten (DE); René Krupka, Haar (DE); Jan Prochnow, Zurich (CH)

(73) Assignee: Rohde & Schwarz GmbH & Co. KG, Munich (DE)

( * ) Notice: Subject to any disclaimer, the term of this patent is extended or adjusted under 35 U.S.C. 154(b) by 0 days.

(21) Appl. No.: 12/995,965

(22) PCT Filed: Jun. 2, 2009

(86) PCT No.: PCT/EP2009/003922
§ 371 (c)(1),
(2), (4) Date: Mar. 17, 2011

(87) PCT Pub. No.: WO2009/146882
PCT Pub. Date: Dec. 10, 2009

(65) Prior Publication Data
US 2011/0160579 A1 Jun. 30, 2011

(30) Foreign Application Priority Data

Jun. 2, 2008 (DE) .......................... 10 2008 026 436
Dec. 22, 2008 (DE) .......................... 10 2008 064 400

(51) Int. Cl.
*A61B 5/00* (2006.01)
*A61B 5/05* (2006.01)

(52) U.S. Cl.
CPC ............... *A61B 5/05* (2013.01); *A61B 5/0507* (2013.01)
USPC .......................................... 600/430; 60/431

(58) Field of Classification Search
USPC ........................................ 600/407, 430, 431
See application file for complete search history.

(56) References Cited

U.S. PATENT DOCUMENTS

| 4,684,894 A * | 8/1987 | Bliehall ...................... 324/318 |
| 4,719,425 A | 1/1988 | Ettinger |
| 4,889,942 A | 12/1989 | Gutek |
| 5,807,257 A * | 9/1998 | Bridges ...................... 600/430 |

(Continued)

FOREIGN PATENT DOCUMENTS

| DE | 44 33 572 A1 | 4/1995 |
| DE | 690 23 532 T2 | 5/1996 |
| EP | 0 351 919 A1 | 7/1989 |
| EP | 0 361 551 A1 | 7/1989 |

(Continued)

OTHER PUBLICATIONS

International Search Report mailed Sep. 2, 2009, in corresponding International Application No. PCT/EP2009/003922, filed Jun. 2, 2009.

(Continued)

*Primary Examiner* — Ruth S Smith
(74) *Attorney, Agent, or Firm* — Christensen O'Connor Johnson Kindness PLLC

(57) ABSTRACT

A device for the investigation of an object uses a microwave transmitter, a microwave receiver, a control device and a contrast medium. The microwave transmitter and the microwave receiver are controlled by the control device. In one embodiment, the following steps may be implemented:
 introduction of the contrast medium into the object under investigation;
 transmission of a microwave signal into the object under investigation by the microwave transmitter;
 scattering of the microwave signal by the object under investigation and by the contrast medium; and/or
 reception of the scattered microwave signal by the microwave receiver.

19 Claims, 3 Drawing Sheets

(56) References Cited

U.S. PATENT DOCUMENTS

| | | | |
|---|---|---|---|
| 8,095,204 B2 * | 1/2012 | Smith et al. | 600/430 |
| 2003/0016032 A1 | 1/2003 | Licini | |
| 2004/0077943 A1 * | 4/2004 | Meaney et al. | 600/430 |
| 2006/0022675 A1 | 2/2006 | Blank | |
| 2006/0083689 A1 * | 4/2006 | Haroon et al. | 424/9.351 |
| 2006/0293586 A1 | 12/2006 | Hillenbrand | |

FOREIGN PATENT DOCUMENTS

| | | |
|---|---|---|
| EP | 0 928 157 B1 | 7/1997 |
| WO | 2006/116021 A2 | 11/2006 |

OTHER PUBLICATIONS

Jones, J.B., "The Profile Distribution of Total and Extractable Copper in Selected Nigerian Soils," Communications in Soil Science and Plant Analysis 10(11)1385-1397, Ref No. XP008125959, Marcel Dekker, Inc., 1979.

Rumyantseva, G.V., et al., "Trace Transition Metal-Catalyzed Reactions in the Microsomal Metabolism of Alkyl Hydrazines to Carbon-Centered Free Radicals," The Journal of Biological Chemistry 266(32):21422-21427, 1991.

Spanoghe, M., et al., "Proton Relaxation Enhancement by Means of Serum Albumin and Poly-L-Lysine Labeled with DTPA-Gd3+: Relaxivities as a Function of Molecular Weight and Conjugation Efficiency," Magnetic Resonance Imaging 10:913-917, 1992.

Runge, V., et al., "Gd DTPA: A Review of Clinical Indications in Central Nervous System Magnetic Resonance Imaging," RadioGraphics 9(5):929-58, Sep. 1989.

Office Action mailed Mar. 26, 2014, issued in related European Application No. 09757265.5, filed Jun. 2, 2009, 4 pages.

* cited by examiner

MICROWAVE INVESTIGATION WITH A CONTRAST MEDIUM

FIELD OF THE INVENTION

The invention relates to a method, a contrast medium and the use of a contrast medium for microwave-based investigation.

BACKGROUND

In some cases, the dielectric constants of objects under investigation, especially living tissue, are very homogeneous, and reliable results which can be presented with a clear contrast cannot always be attained with conventional microwave-based investigations.

Magnetic-resonance tomographies are prepared as an alternative. With the help of contrast media, more accurate results can be obtained. However, the preparation of magnetic-resonance tomographies is associated with high costs. Furthermore, in the case of patients in intensive care, an investigation of this kind is possible only with difficulty.

Accordingly, DE 44 33 572 A1 discloses the use of gadolinium-diethylene-triamino-penta-acetate (Gd-DPTA) as a contrast medium for magnetic-resonance investigations.

SUMMARY

A measuring device according to the invention comprises a microwave transmitter, a microwave receiver, a control device, a contrast medium and an electromagnet. The control device controls the microwave transmitter, the microwave receiver and the electromagnet. The contrast medium is introduced into an object under investigation. The electromagnet provides the object under investigation with a magnetic field. The contrast medium changes its polarisation properties dependent upon the field strength of the magnetic field. The microwave transmitter transmits a microwave signal. The object under investigation and the contrast medium scatter the microwave signal. The contrast medium changes a polarisation of the microwave signal. The microwave receiver receives the scattered microwave signal changed in its polarisation. Accordingly, a low-stress investigation of the object can be implemented at low cost.

The microwave transmitter and/or the microwave receiver preferably focus successively on several locations within the object under investigation. In this manner, a good local resolution can be achieved.

The control device preferably determines a microwave topography from the received microwave signal. In this manner, a detailed, three-dimensional image is achieved.

According to the invention, a contrast medium is used in the microwave-based investigation of an object. The contrast medium is introduced into the object under investigation. By comparison with its surroundings in the object under investigation, the contrast medium provides a different permittivity and/or conductivity and/or polarisation effect. Accordingly, an increase in the accuracy of the microwave-based investigation is achieved.

The contrast medium preferably comprises a paramagnetic metal ion, preferably a gadolinium ion ($Gd^{3+}$) or an iron ion ($Fe^{3+}$) or aluminium ion ($Al^{3+}$) or a technetium ion ($Tc^{3+}$). A particularly good improvement in accuracy can be achieved in this manner. Although the use of technetium ions brings about a clear increase in accuracy, it is disadvantageous that technetium is slightly radioactive and therefore causes radiation stress in the object under investigation. A cost-benefit assessment must therefore be implemented before a use of technetium.

The contrast medium preferably contains a coordinative bond. In this manner, a very stable structure of the contrast medium can be achieved. In particular, a good biocompatibility is achieved in this manner.

The contrast medium advantageously comprises gadolinium and/or a gadolinium compound and/or gadolinium-diethylene-triamino-penta-acetate (Gd-DTPA). Readily available contrast media can therefore be used.

The polarising effect of the contrast medium is preferably intensified or attenuated by an applied magnetic field. Polarising effects of the object under investigation can therefore be compensated.

A method according to the invention for investigating an object uses a microwave transmitter, a microwave receiver, a control device and a contrast medium. The microwave transmitter and the microwave receiver are controlled by the control device. The following steps are implemented:
  introduction of the contrast medium into the object under investigation;
  transmission of a microwave signal into the object under investigation;
  scattering of the microwave signal by the object under investigation and by the contrast medium; and
  reception of the scattered microwave signal by the microwave receiver. A good accuracy of the investigation is achieved in this manner with low stress on the object under investigation.

The object under investigation is preferably a tissue of a patient. The contrast medium is preferably injected or swallowed. The contrast medium is preferably enriched in given regions of the tissue. The given regions of the tissue are preferably tumours. Accordingly, a high-precision investigation and detection of tumours is possible.

By preference, an external magnetic field is applied. The external magnetic field intensifies or attenuates a polarising effect of the contrast medium. A further increase in the contrast and accordingly of the measurement accuracy is achieved.

During the investigation, the external magnetic field preferably successively adopts at least two different field strengths. In this manner, a comparative measurement can be implemented. Polarising effects of the tissue can thus be eliminated.

DESCRIPTION OF THE DRAWINGS

The invention is described in an exemplary manner below on the basis of the drawings, in which an advantageous exemplary embodiment of the invention is illustrated. The drawings are as follows.

DETAILED DESCRIPTION

Figure 1:
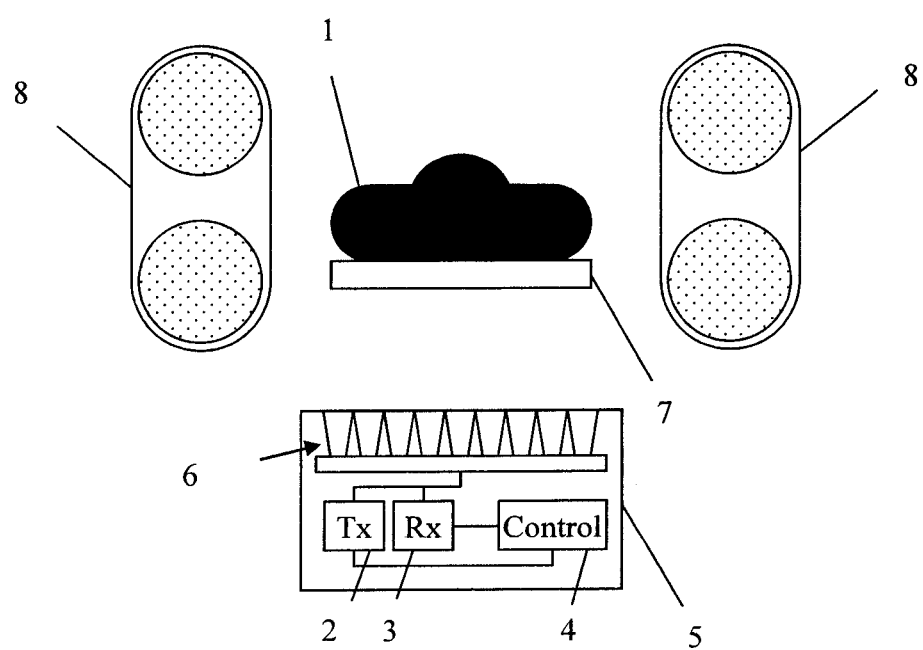
FIG. 1 shows an exemplary embodiment of the measuring device according to the invention.
Figure 2:
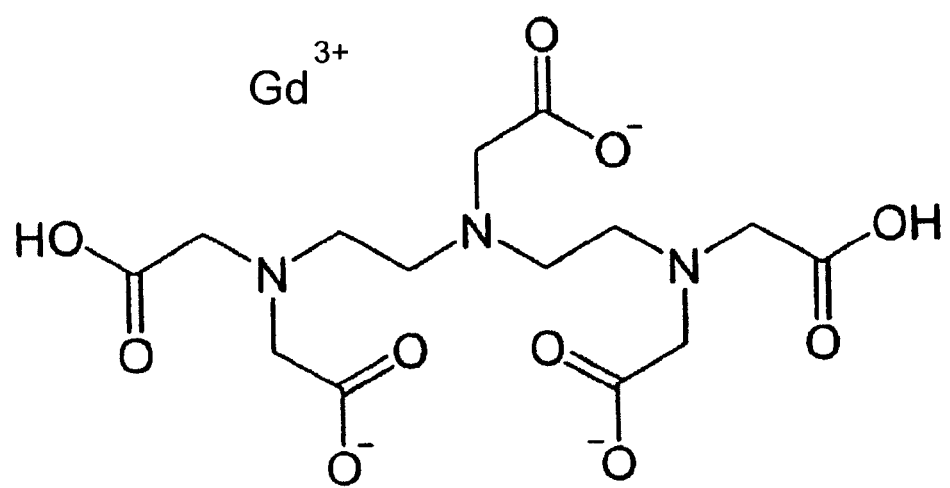
FIG. 2 shows a structural formula of an exemplary contrast medium.

The structure and functioning of the measuring device are initially explained on the basis of FIG. 1. With reference to FIG. 2, the structure of an exemplary contrast medium is illustrated. Finally, on the basis of FIG. 3, the functioning of the method according to the invention is shown. The presentation and description of identical elements in similar drawings has in some cases not been repeated.

FIG. 1 shows an exemplary embodiment of the measuring device according to the invention. A patient 1 lies on a patient support 7. Electromagnets 8 are arranged alongside the patient 1. A housing 5 is arranged below the patient 1. The housing 5 contains a microwave transmitter 2, a microwave receiver 3, an antenna array 6 and a control device 4. The microwave transmitter 2 and the microwave receiver 3 in this context are each connected to the antenna array 6 and to the control device 4. The control device 4 controls the microwave transmitter 2, the microwave receiver 3 and the electromagnets 8.

The object under investigation in this exemplary embodiment is a tissue of the patient 1. In order to implement an investigation, a contrast medium is first injected into the object under investigation. In this exemplary embodiment, the contrast medium is introduced into the tissue or into a blood vessel by injection. The microwave transmitter 2 transmits a microwave signal into the tissue of the patient 1 by means of the antenna array 6. The microwave signal is scattered by the tissue and/or by the contrast medium. A repolarisation of the microwave signal can be additionally implemented by the contrast medium. The possibly repolarised and scattered microwave signal is received by the microwave receiver 3 by means of the antenna array 6.

An alignment of the contrast medium within the magnetic field is achieved by activating the electromagnets 8. Through this alignment, the polarisation properties of the contrast medium change. The method presented above is repeated for at least one field strength of the magnetic field. The accuracy can be further increased through additional repetitions with different field strengths of the magnetic field.

The control device 4 determines a microwave tomography from the received microwave signals. Since the contrast medium is not distributed homogeneously in the object under investigation but is enriched in an intensified manner in given regions, an improvement in accuracy is achieved especially in these regions. In this exemplary embodiment, the regions are regions with a particularly strong blood circulation, which indicates the presence of tumours. The detection of other pathologically altered tissue changes is achieved in this manner.

The contrast medium is a substance, which provides a different conductivity and/or dielectric constant and/or polarisation effect by comparison with the object under investigation, here, the human tissue. Biocompatibility is especially necessary in this exemplary embodiment.

The use of the contrast medium to improve the measurement accuracy in microwave-based investigations is also possible without the participation of a magnetic field; repolarisation does not then take place.

FIG. 2 illustrates the structural formula of an exemplary contrast medium. The contrast medium is gadolinium-diethylene-triamino-penta-acetate (Gd-DTPA). That is to say, a trivalent gadolinium cation (Gd3+) is disposed in a coordinative bond with diethylene-triamino-penta-acetate (DTPA). This provides a very stable, biocompatible contrast medium. A coordinative bond of diethylene-triamino-penta-acetate (DTPA) with another paramagnetic metal ion is also possible.

In this context, a first carbon atom is bound via a single bond to a central nitrogen atom. Two hydrogen atoms and a second carbon atom are bound to the first carbon atom. A first oxygen atom is bound to the second carbon atom by means of a double bond. A second oxygen atom is also bound to the second carbon atom by means of a single bond. The second oxygen atom accordingly provides a negative charge.

Furthermore, two identical structures are bound to the central nitrogen atom. One of these structures is described below. A third carbon atom is bound to the central nitrogen atom by means of a single bond. The third carbon atom is bound to two hydrogen atoms and by means of a single bond to a fourth carbon atom. The fourth carbon atom is bound to two hydrogen atoms and by means of a single bond to a second nitrogen atom.

The second nitrogen atom is bound by means of a single bond to a fifth carbon atom. The fifth carbon atom is bound to two hydrogen atoms and by means of a single bond to a sixth carbon atom. The sixth carbon atom is bound by means of a double bond to a third oxygen atom. The sixth carbon atom is a further bound by means of a single bond to a fourth oxygen atom. The fourth oxygen atom accordingly provides a negative charge.

The second nitrogen atom is further bound to a seventh carbon atom. The seventh carbon atom is bound to two hydrogen atoms and an eighth carbon atom. The eighth carbon atom is bound by means of a single bond to a fifth oxygen atom. The fifth oxygen atom is bound to a hydrogen atom. Furthermore, the eighth carbon atom is bound by means of a double bond to a sixth oxygen atom.

The negative charges of the oxygen atoms form a coordinative bond with a trivalent gadolinium cation. As an alternative, other trivalent paramagnetic cations can be used instead of the gadolinium ion. For example, iron ions, aluminium ions or technetium ions can be used. However, the use of technetium is disadvantageous because technetium is slightly radioactive and accordingly causes a radiation stress on the object under investigation.

Figure 3:
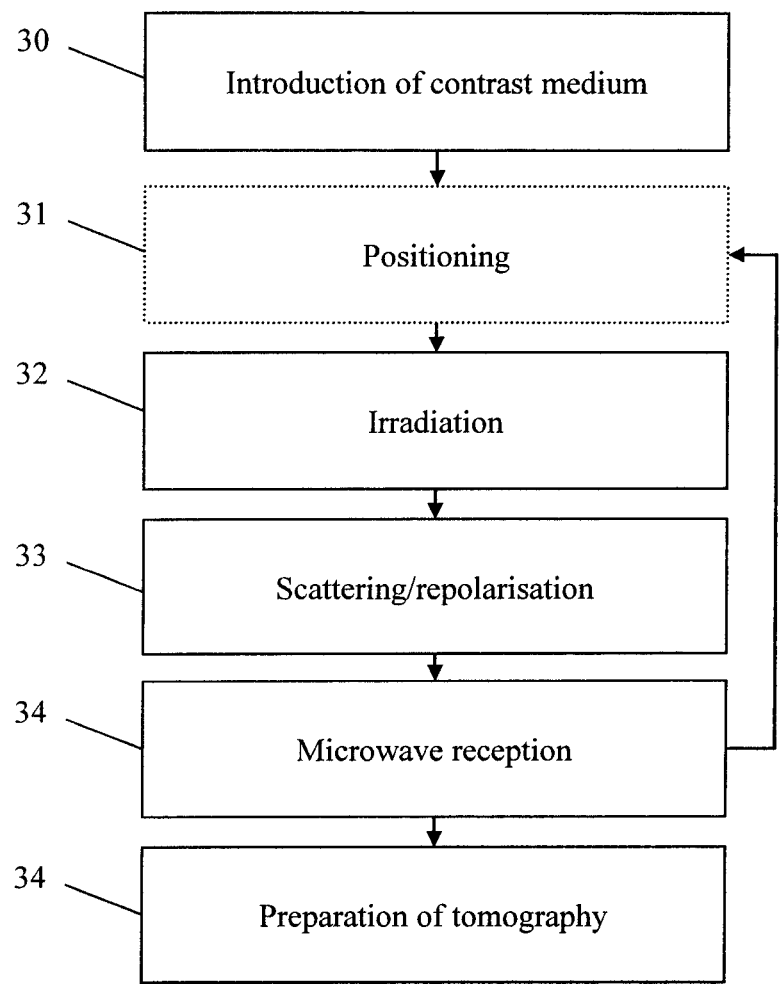
FIG. 3 shows a flow diagram of an exemplary embodiment of the method according to the invention.

FIG. 3 shows a flow chart of an exemplary embodiment of the method according to the invention. In a first step 30, the contrast medium is introduced into the object under investigation. For example, if the object under investigation is human tissue, as illustrated in FIG. 1, the introduction is implemented by injection or orally by swallowing. In an optional second step 31, the object under investigation is positioned opposite to an antenna. Different locations within the object under investigation can be investigated in this manner. As an alternative, different locations within the object under investigation can be investigated through the use of an antenna array, as illustrated in FIG. 1. In a third step 32, the object under investigation or respectively given locations within the object under investigation is/are supplied with microwave signals.

In a fourth step 33, the microwave signal is scattered by the object under investigation or respectively by the contrast medium and possibly repolarised. In a fifth step 34, the scattered, possibly repolarised microwave signal is received. The optional second step 31 is repeated for different locations within the object under investigation up to step 34. In a sixth step 35, a microwave tomography is determined from the received microwave signal or the received microwave signals.

A further increase in accuracy can be achieved by the application of a magnetic field with the use of a corresponding contrast medium. This is illustrated in greater detail on the basis of FIG. 1.

The invention is not restricted to the exemplary embodiment illustrated. As already mentioned, different contrast media can be used. An investigation of an extremely diverse range of objects is also possible. For example, material testing is one conceivable area of application. All of the features described above or illustrated in drawings can be advantageously combined with one another as required within the framework of the invention.

The invention claimed is:

1. A measuring device, comprising:
    a support surface configured to support an object under investigation;
    a microwave antenna positioned below the support surface and an object under investigation when supported by the support surface;
    a microwave transmitter coupled to the microwave antenna, wherein the microwave transmitter is configured to transmit a microwave signal into the object under investigation, the object under investigation capable of scattering the microwave signal;
    a contrast medium capable of being introduced into the object under investigation, wherein the contrast medium is configured to: (1) scatter the microwave signal transmitted into the object under investigation; and (2) change a polarization of the microwave signal transmitted into the object under investigation;
    a microwave receiver coupled to the microwave antenna, wherein the microwave receiver is configured to receive the microwave signal scattered by at least the object under investigation and changed in its polarization; and
    a control device connected to the microwave transmitter and the microwave receiver in such a manner that it controls the microwave transmitter and the microwave receiver, wherein the control device is configured to generate a microwave tomography from the received microwave signal, and wherein the microwave transmitter and the microwave receiver are configured to focus successively on several locations within the object under investigation.

2. The measuring device according to claim 1, wherein the antenna includes an antenna array.

3. The measuring device according to claim 1, wherein the microwave tomography is generated independently of a magnetic field applied to the object under investigation.

4. The measuring device according to claim 1, further comprising an electromagnet configured to provide a magnetic field to the object under investigation solely for intensifying or attenuating a polarization effect of the contrast medium.

5. A method of using a contrast medium in a microwave-based investigation of an object, comprising:
    introducing a contrast medium into an object under investigation, wherein the contrast medium provides one or more of a different permittivity, conductivity, and polarization effect from its surroundings within the object under investigation;
    positioning the object under investigation opposite an antenna;
    transmitting a microwave signal from the antenna into the object under investigation;
    scattering the microwave signal by at least the contrast medium;
    receiving the scattered microwave signal by the antenna; and
    generating a microwave tomography from the scattered microwave signal,
    wherein one of said transmitting a microwave signal and said receiving the scattered microwave includes focusing the antenna successively on several locations within the object under investigation.

6. The method according to claim 5, wherein the contrast medium contains a paramagnetic metal ion.

7. The method of use according to claim 6, wherein the paramagnetic metal ion is selected from a group consisting of a gadolinium ion ($Gd^{3+}$), an iron ion ($Fe^{3+}$), an aluminum ion ($Al^{3+}$), and a technetium ion ($Tc^{3+}$).

8. The method according to claim 5, wherein the contrast medium includes a coordinative bond.

9. The method according to claim 5, wherein the contrast medium includes gadolinium, a gadolinium compound, or gadolinium-diethylene-triamino-penta-acetate (Gd-DTPA).

10. The method according to claim 5, wherein the contrast medium provides the following structure:

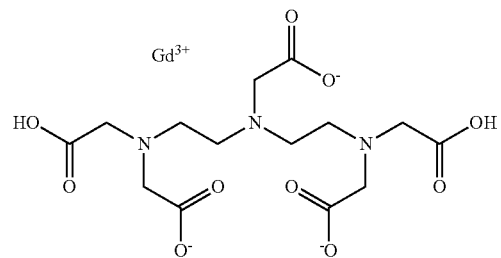

wherein
N denotes a nitrogen atom,
O denotes an oxygen atom,
H denotes a hydrogen atom and
Gd3+ denotes a trivalent cation of gadolinium.

11. The method according to claim 5, wherein the antenna includes an antenna array.

12. A method for investigating an object with a microwave transmitter, a microwave receiver, a control device, an antenna coupled to the microwave transmitter and the microwave receiver, and a contrast medium, wherein the microwave transmitter and the microwave receiver are controlled by the control device, the method comprising:
    introducing the contrast medium into an object under investigation;
    positioning the object under investigation opposite the antenna;
    transmitting a microwave signal into the object under investigation by the microwave transmitter;
    scattering of the microwave signal by the object under investigation and by the contrast medium;
    receiving the scattered microwave signal by the microwave receiver; and
    generating a microwave tomography from the scattered microwave signal,
    wherein the transmitted microwave signal and the received microwave signal are focused successively on several locations within the object under investigation.

13. The method according to claim 12, wherein
    the object under investigation is tissue,
    the contrast medium is injected or swallowed, and
    the contrast medium is enriched in given regions of the tissue, and that the given regions are tumors.

14. The method according to claim 12 wherein the contrast medium includes a paramagnetic metal ion.

15. The method according to claim 14, wherein the paramagnetic metal ion is selected from a group consisting of a gadolinium ion ($Gd^{3+}$), an iron ion ($Fe^{3+}$), an aluminum ion ($Al^{3+}$), and a technetium ion ($Tc^{3+}$).

16. The method according to claim 12,
    wherein the contrast medium provides one or more of: a different permittivity, conductivity, and polarization effect from its surroundings in the object under investigation.

17. The method according to claim 12,
wherein an external magnetic field is applied,
wherein the external magnetic field intensifies or attenuates a polarizing effect of the contrast medium, and
wherein the external magnetic field includes at least two different strengths, and wherein during the investigation, the at least two different strengths of the external magnetic field are successively applied.

18. The method according to claim 12, wherein the antenna includes an antenna array.

19. The method according to claim 12, wherein the contrast medium includes gadolinium, a gadolinium compound, or gadolinium-diethylene-triamino-penta-acetate (Gd-DTPA).

* * * * *